US010213783B2

(12) United States Patent
Chen et al.

(10) Patent No.: US 10,213,783 B2
(45) Date of Patent: Feb. 26, 2019

(54) NUCLEIC ACID EXTRACTING DEVICE

(71) Applicant: DELTA ELECTRONICS, INC., Taoyuan (TW)

(72) Inventors: Wang-Chu Chen, Taoyuan (TW); Song-Bin Huang, Taoyuan (TW)

(73) Assignee: Delta Electronics, Inc., Taoyuan (TW)

( * ) Notice: Subject to any disclaimer, the term of this patent is extended or adjusted under 35 U.S.C. 154(b) by 0 days.

(21) Appl. No.: 15/018,067

(22) Filed: Feb. 8, 2016

(65) Prior Publication Data

US 2017/0015993 A1    Jan. 19, 2017

(30) Foreign Application Priority Data

Jul. 17, 2015    (TW) .............................. 104123190 A

(51) Int. Cl.
*C12N 15/10* (2006.01)
*B01L 3/00* (2006.01)
*G01N 1/40* (2006.01)

(52) U.S. Cl.
CPC ......... *B01L 3/508* (2013.01); *B01L 3/502715* (2013.01); *B01L 3/527* (2013.01); *B01L 3/563* (2013.01); *G01N 1/405* (2013.01); *B01L 2200/10* (2013.01); *B01L 2200/16* (2013.01); *B01L 2400/0487* (2013.01)

(58) Field of Classification Search
CPC .... B01L 3/508; B01L 3/502715; B01L 3/527; B01L 3/563; G01N 1/34
USPC ........................................................ 422/527
See application file for complete search history.

(56) References Cited

U.S. PATENT DOCUMENTS

| 7,192,559 B2 * | 3/2007 | Chow ................... B01D 61/18 137/87.01 |
| 2005/0045538 A1 | 3/2005 | Seto et al. |
| 2005/0142571 A1 | 6/2005 | Parthasarathy et al. |
| 2006/0019379 A1 * | 1/2006 | Taylor ................... B01L 3/5027 435/306.1 |
| 2006/0110725 A1 | 5/2006 | Lee et al. |

(Continued)

FOREIGN PATENT DOCUMENTS

| CN | 101765463 A | 6/2010 |
| TW | 201326814 A1 | 7/2013 |

(Continued)

*Primary Examiner* — Jill A Warden
*Assistant Examiner* — Jacquelne Brazin
(74) *Attorney, Agent, or Firm* — Muncy, Geissler, Olds & Lowe, P.C.

(57) ABSTRACT

A nucleic acid extracting device includes an upper module, a lower module, and a material for capturing nucleic acid. The lower module has a sample reservoir receiving a sample, an elution reservoir receiving an elution, and a nucleic acid capturing chamber with the material disposed therein. The upper module has a sample channel that communicates with the sample reservoir, and an elution channel that communicates with the elution reservoir. The nucleic acid capturing chamber communicates with the sample channel and the elution channel. When a sample enters the nucleic acid capturing chamber via the sample channel, a nucleic acid in the sample is absorbed by the material in the nucleic acid capturing chamber, and the elution enters the nucleic acid capturing chamber, via the elution channel, to wash the nucleic acid out of the nucleic acid capturing chamber.

10 Claims, 11 Drawing Sheets

(56) References Cited

U.S. PATENT DOCUMENTS

| | | |
|---|---|---|
| 2006/0172642 A1 | 8/2006 | Sasaki et al. |
| 2008/0121591 A1 | 5/2008 | Knight et al. |
| 2009/0148933 A1 | 6/2009 | Battrell et al. |
| 2010/0216225 A1 | 8/2010 | Dyer et al. |
| 2014/0206073 A1 | 7/2014 | Park et al. |

FOREIGN PATENT DOCUMENTS

| | | |
|---|---|---|
| WO | WO 2005/073691 A1 | 8/2005 |
| WO | WO 2005/111210 A1 | 11/2005 |
| WO | WO 2006/032044 A2 | 3/2006 |
| WO | WO 2007/149791 A2 | 12/2007 |
| WO | WO 2008/149111 A1 | 12/2008 |
| WO | WO 2010/091080 A2 | 8/2010 |

\* cited by examiner

NUCLEIC ACID EXTRACTING DEVICE

CROSS REFERENCE TO RELATED APPLICATIONS

This Application claims priority of Taiwan Patent Application No. 104123190, filed on Jul. 17, 2015, the entirety of which is incorporated by reference herein.

BACKGROUND OF THE INVENTION

Field of the Invention

Aspects of the present invention relate generally to extracting devices, and more particularly, to nucleic acid extracting devices.

Description of the Related Art

As technologies progress and international travel has become more convenient, the rapid spread of infectious diseases, such as SARS, avian influenza, and dengue fever, had become global threats. Nowadays, a common way to conduct preliminary disease detection within 30 minutes is through a rapid diagnostic test. Detection accuracy is not good enough, however. Conventional molecular diagnosis may achieve high accuracy in detection, but the instrument is expensive, and its operation is complicated.

BRIEF SUMMARY OF THE INVENTION

In one exemplary embodiment, a nucleic acid extracting device is provided in the invention. The nucleic acid extracting device includes an upper module, a lower module, and a material for capturing nucleic acid. The lower module has a sample reservoir, an elution reservoir, and a nucleic acid capturing chamber, wherein a sample is received in the sample reservoir, and an elution is received in the elution reservoir. The material for capturing nucleic acid is disposed in the nucleic acid capturing chamber. The upper module has a sample channel that communicates with the sample reservoir, and an elution channel that communicates with the elution reservoir, wherein the nucleic acid capturing chamber communicates with the sample channel and the elution channel. When the sample enters the nucleic acid capturing chamber via the sample channel, a nucleic acid in the sample is absorbed by the material, and the elution enters the nucleic acid capturing chamber via the elution channel to wash the nucleic acid out of the nucleic acid capturing chamber.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

While the invention has been described in connection with various aspects, it will be understood that the invention is capable of further modifications. This application is intended to cover any variations, uses or adaptation of the invention following, in general, the principles of the invention, including such departures from the present disclosure as come within the known and customary practice within the art to which the invention pertains.

In the following detailed description of the preferred embodiments, reference is made to the accompanying drawings, and in which specific embodiments of which the invention may be practiced are shown by way of illustration. In this regard, directional terminology, such as "top," "bottom," "front," "back," etc., is used with reference to the orientation of the Figure(s) being described. The components of the present invention can be positioned in a number of different orientations. As such, the directional terminology is used for purposes of illustration and is in no way limiting.

Figure 1A:
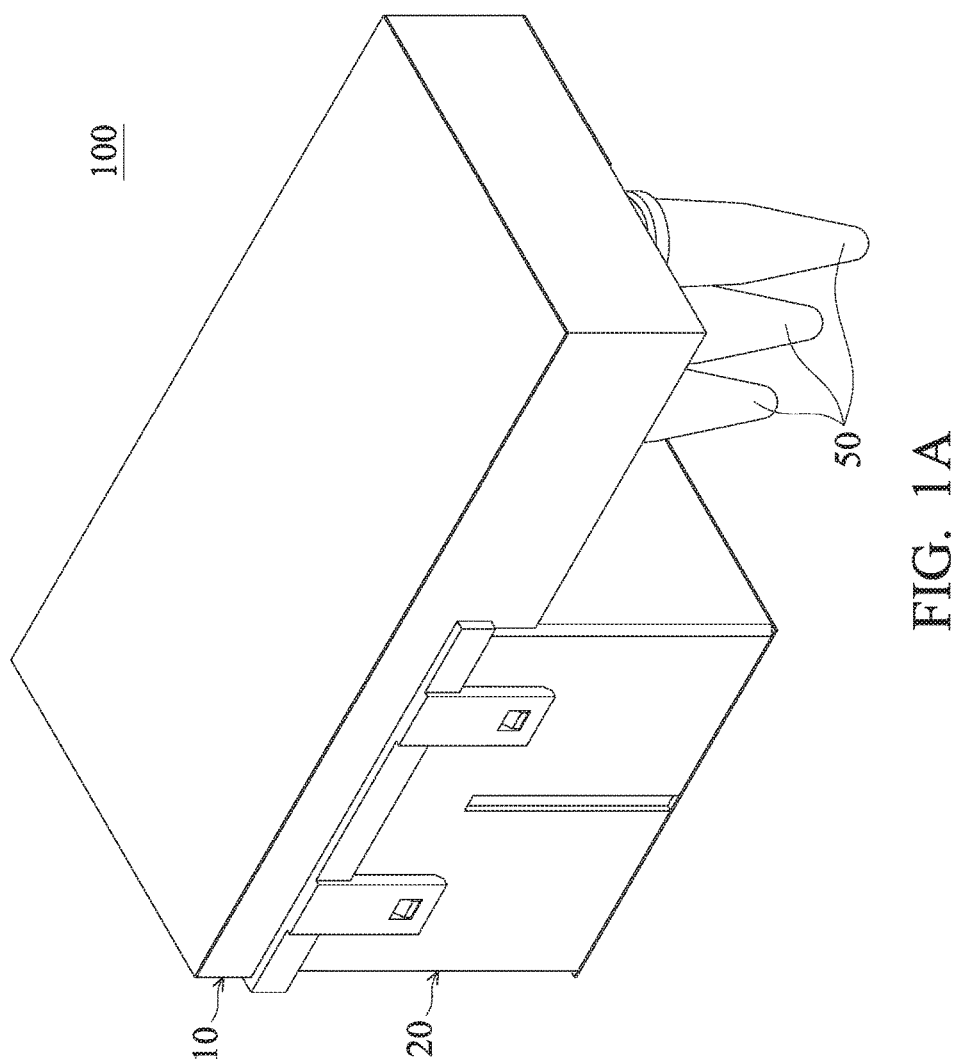
FIG. 1A is a perspective diagram of a nucleic acid extracting device according to one embodiment of the invention.
Figure 1B:
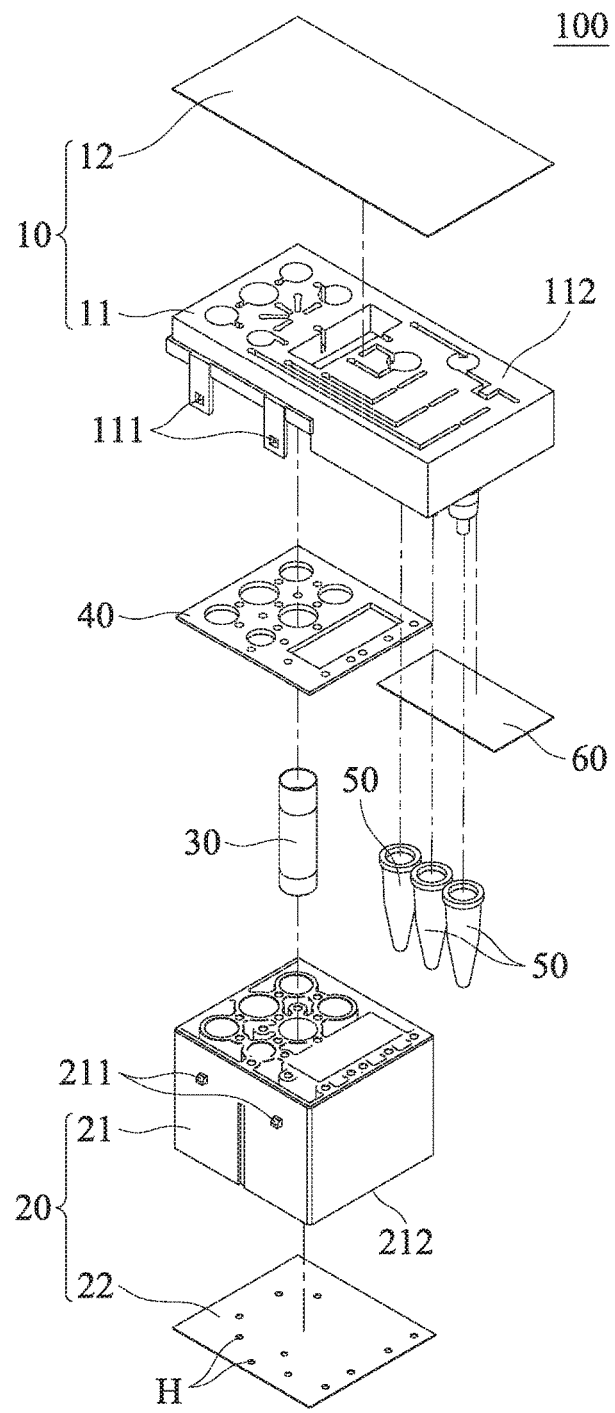
FIG. 1B is an exploded diagram of the nucleic acid extracting device in FIG. 1A.

Referring to FIGS. 1A and 1B, a nucleic acid extracting device 100 according to an embodiment of the invention is used for nucleic acid extraction from an organic sample, such as blood, urine, or saliva. The nucleic acid extracting device 100 primarily comprises an upper module 10, a lower module 20, a hollow member 30, a buffer member 40, at least a container 50, and a cover 60. As shown in FIG. 1B, the buffer member 40 may be a flexible silicon rubber sheet disposed between the upper and lower modules 10 and 20, so as to achieve an airtight seal of the fluid channels in the upper and lower modules 10 and 20. Additionally, several containers 50 are detachably disposed on the bottom of the upper module 10.

In this embodiment, the upper module 10 comprises an upper member 11 and an upper membrane 12, and the lower module 20 comprises a lower member 21 and a lower membrane 22. The upper membrane 12 is adhered to the top surface 112 of the upper member 11, adjacent to the channels on the top surface 112, so as to prevent the fluid in the upper member 11 from leaking via the top surface 112. Similarly, the lower membrane 22 is adhered to a bottom surface 212 of the lower member 21, so as to prevent the fluid in the lower member 21 from leaking via the bottom surface 212. As shown in FIG. 1B, the upper member 11 has a first joining portion 111 (such as a slot), and the lower member 21 has a second joining portion 211 (such as a hook). When connecting or assembling the upper module 10 with the lower module 20, the first and second joining portions 111 and 211 are joined to each other. Moreover, the cover 60 covers the bottom side of the upper member 11 and is located between the upper member 11 and the containers 50.

Since the nucleic acid extracting device 100 in this embodiment has two main parts of the upper and lower modules 10 and 20, nucleic acid elution and cleaner can be previously filled into the reservoirs defined in the lower module 20. When performing nucleic acid extraction, a test sample is loaded to a sample reservoir in the lower module 20, and then the upper and lower modules 10 and 20 are assembled to each other. After the extraction process, the liquid containing nucleic acid can flow through interior channels to the containers 50 for amplification and detection, thus facilitating simple assembly and easy use.

Referring to FIGS. 2A-3D, several channels are formed on the top surface 112 of the upper member 11. In this embodiment, three cleaner channels C1-C3, a sample channel C4, and a elution channel C5 are disposed on the top surface 112, that communicate with corresponding three cleaner reservoirs W1'-W3', a sample reservoir S', and a elution reservoir E' in the lower member 21, respectively. External air can be induced into the lower member 21 via the air holes H on the lower membrane 22 by an air pump, and the air sequentially flows through the through holes H' (FIG. 3C) on the bottom surface 212 of the lower member 21, and the channels W1-W3, S, and E of the upper member 11, such that the cleaner in the cleaner reservoirs W1'-W3', the sample in the sample reservoir S', and the elution in the elution reservoir E' are respectively pushed by the air. Therefore, the cleaner, the sample, and the elution can sequentially flow through the channels C1'-C5' in the lower member 21 and the channels C1-C5 in the upper member 11 to a nucleic acid capturing chamber P' in the lower member 21. In brief, as several air channels are formed and extended through the upper and lower modules 10 and 20, the cleaner, the sample, and the elution can respectively be controlled and pushed by air to the nucleic acid capturing chamber P'. The connective relationship between the channels, the reservoirs, and the nucleic acid capturing chamber P' is presented in a simplified diagram of FIG. 3D.

As depicted in FIGS. 2A-3D, the channels C1'-C5' in the lower member 21 are respectively in communication with the channels C1-C5 in the upper member 11. When the cleaner in the cleaner reservoirs W1'-W3', the sample in the sample reservoir S', and the elution in the elution reservoir E' are pushed by the driving air, these different liquids can respectively flow through the channels C1'-C5' in the lower member 21 to the corresponding channels C1-C5 in the upper member 11. Subsequently, these liquids flow to the nucleic acid capturing chamber P' via a guide portion P on a bottom surface 113 of the upper member 11 (FIG. 2B).

Figure 3A:
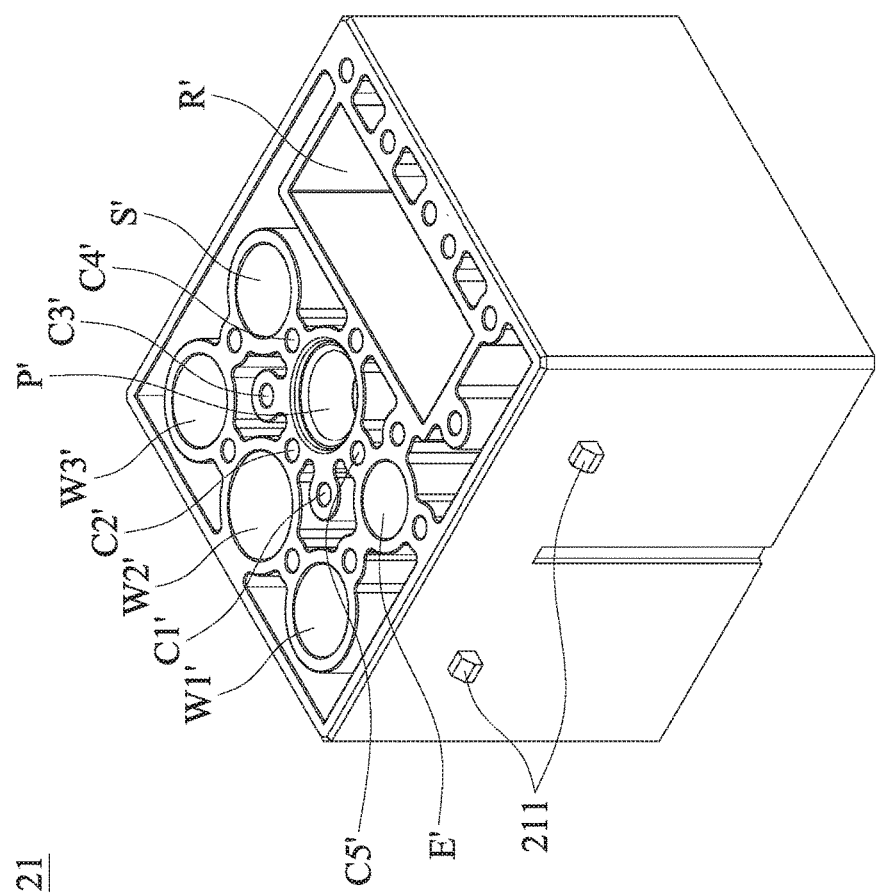
FIG. 3A is a perspective diagram of a lower member according to one embodiment of the invention.
Figure 3B:
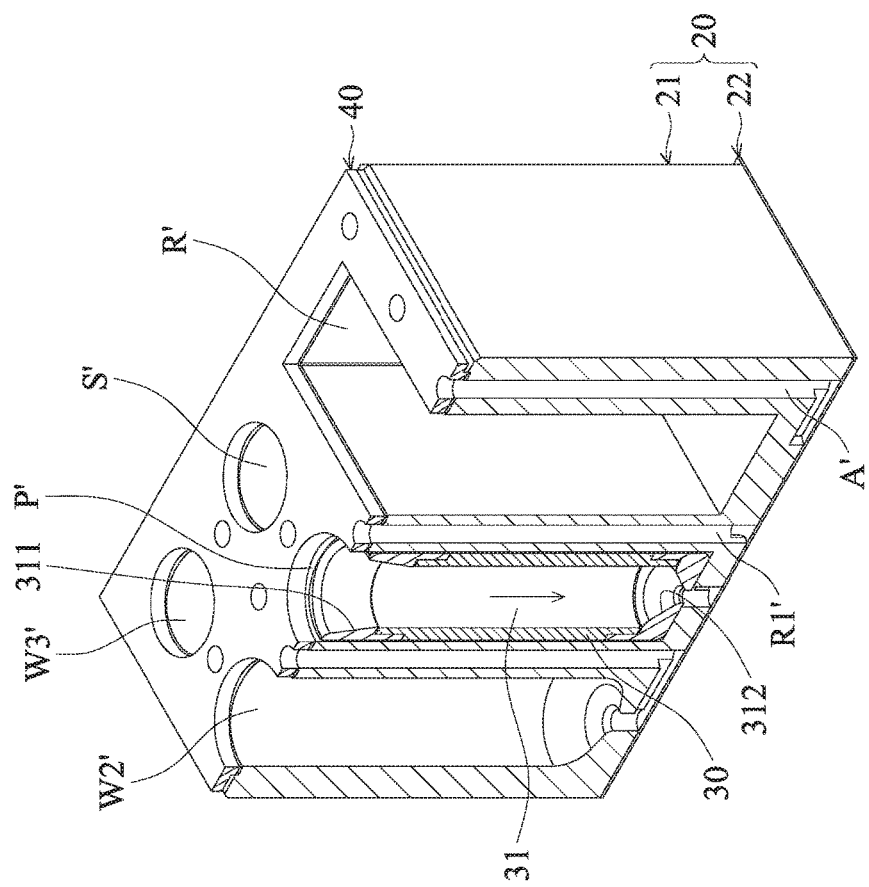
FIG. 3B is a sectional view showing a material for capturing nucleic acid which is disposed in a nucleic acid capturing chamber of the lower member according to one embodiment of the invention.
Figure 3C:
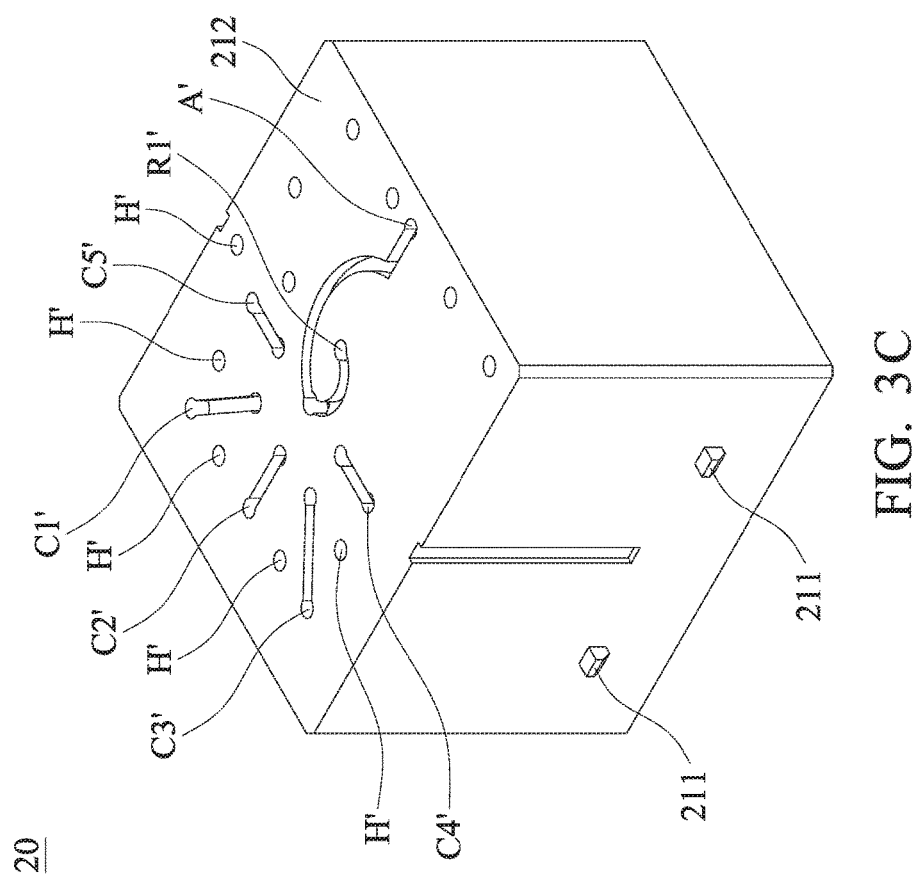
FIG. 3C is another view of the lower member.
Figure 3D:
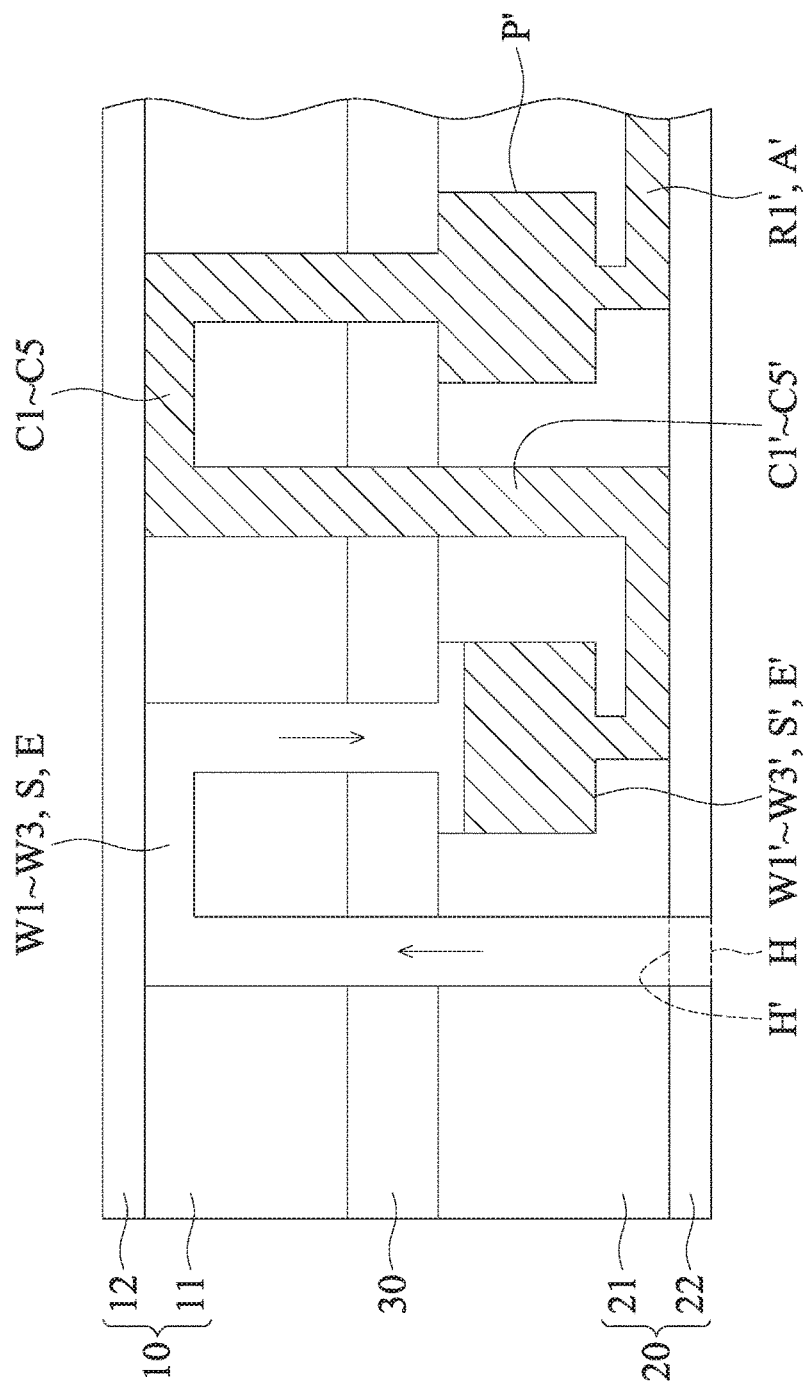
FIG. 3D is perspective diagram showing the connective relationship between the channels, the reservoirs, and the nucleic acid capturing chamber in the upper and lower members.

It can be seen in FIG. 3B that the hollow member 30 is received in the nucleic acid capturing chamber P' in the lower member 21. The hollow member 30 comprises a tubular body 31 with a material disposed therein for capturing nucleic acid. The material adapted for capturing nucleic acid may comprise silica beads, silica membrane, Chitosan Beads, or magnetic beads. It is noted that the tubular body 31 has a tapered inlet 311 and a tapered outlet 312 which are tapered along the flow direction (from top to bottom). When the sample flows through the hollow member 30, the nucleic acid can be adsorbed by the material in the tubular body 31 for nucleic acid extraction. However, in some embodiments, the material for capturing nucleic acid can also be directly disposed in the nucleic acid capturing chamber P' without the hollow member 30.

For example, when using the nucleic acid extracting device 100, firstly, the sample liquid in the sample reservoir S' can be driven by an air pump to the nucleic acid capturing chamber P'. The next step is to drive the cleaner in the cleaner reservoirs W1'-W3' flowing through the channels C1-C3 to the nucleic acid capturing chamber P' by the air pump, so as to wash the non-nucleic acid substance out of the sample. After washing off the non-nucleic acid substance, the cleaner flows from the nucleic acid capturing chamber P' through a channel R1' underneath the lower member 21 (FIGS. 3B and 3C) to a waste liquid channel C6 in the upper member 11 (FIG. 2A), and then flows to a waste liquid reservoir R' in the lower member 21. Finally, the elution in the elution reservoir E' can be driven though the elution channel C5 to the nucleic acid capturing chamber P', such that the nucleic acid is extracted from the material. Subsequently, the elution with extracted nucleic acid flows through a nucleic acid collection channel A' (FIGS. 3A and 3B) in lower member 21 to a nucleic acid collection reservoir A in the upper member 11 (FIG. 2A), such that the liquid with the extracted nucleic acid in the nucleic acid collection reservoir A can be dropped to the containers 50 for amplification and detection.

Figure 2A:
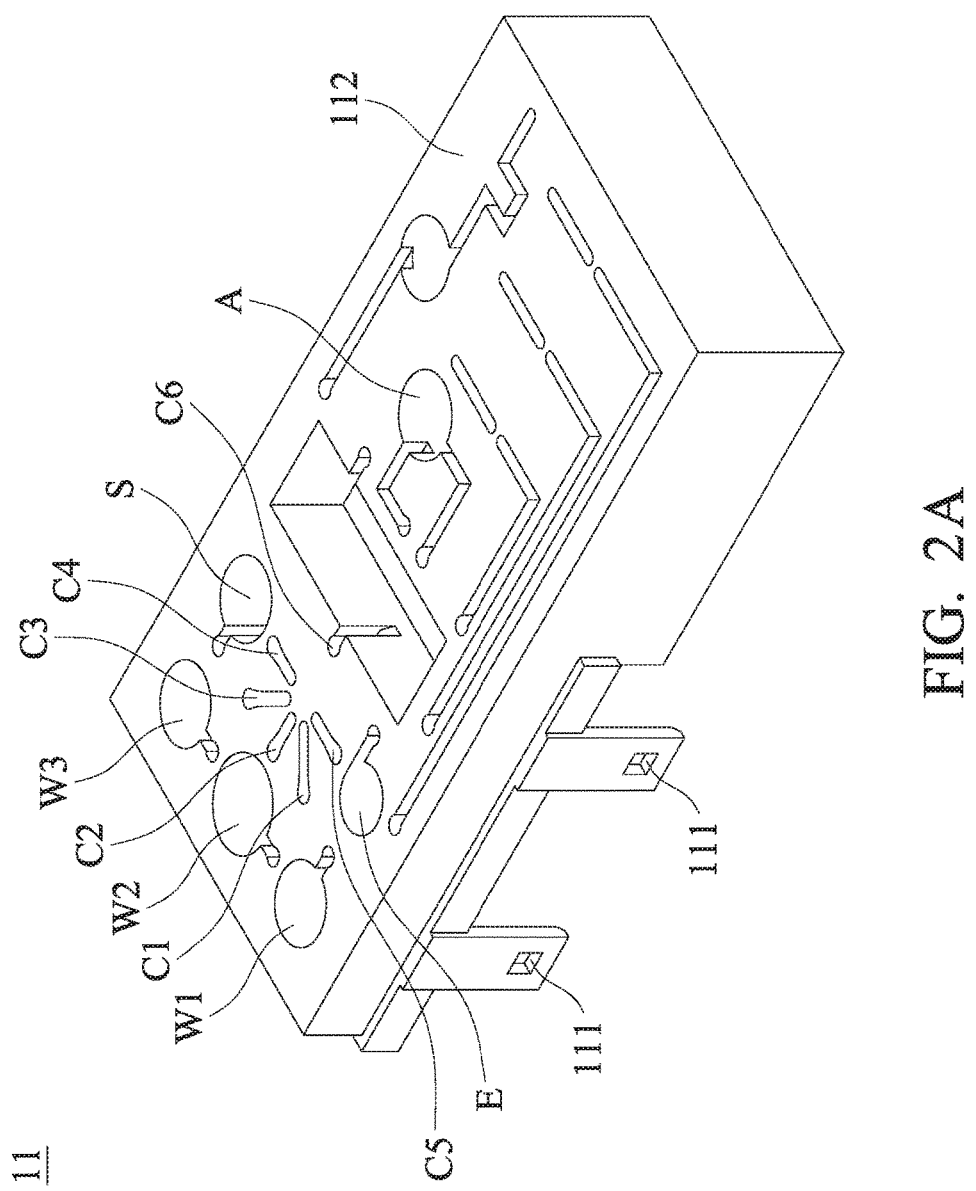
FIGS. 2A and 2B are perspective diagrams of an upper member according to one embodiment of the invention.
Figure 2B:
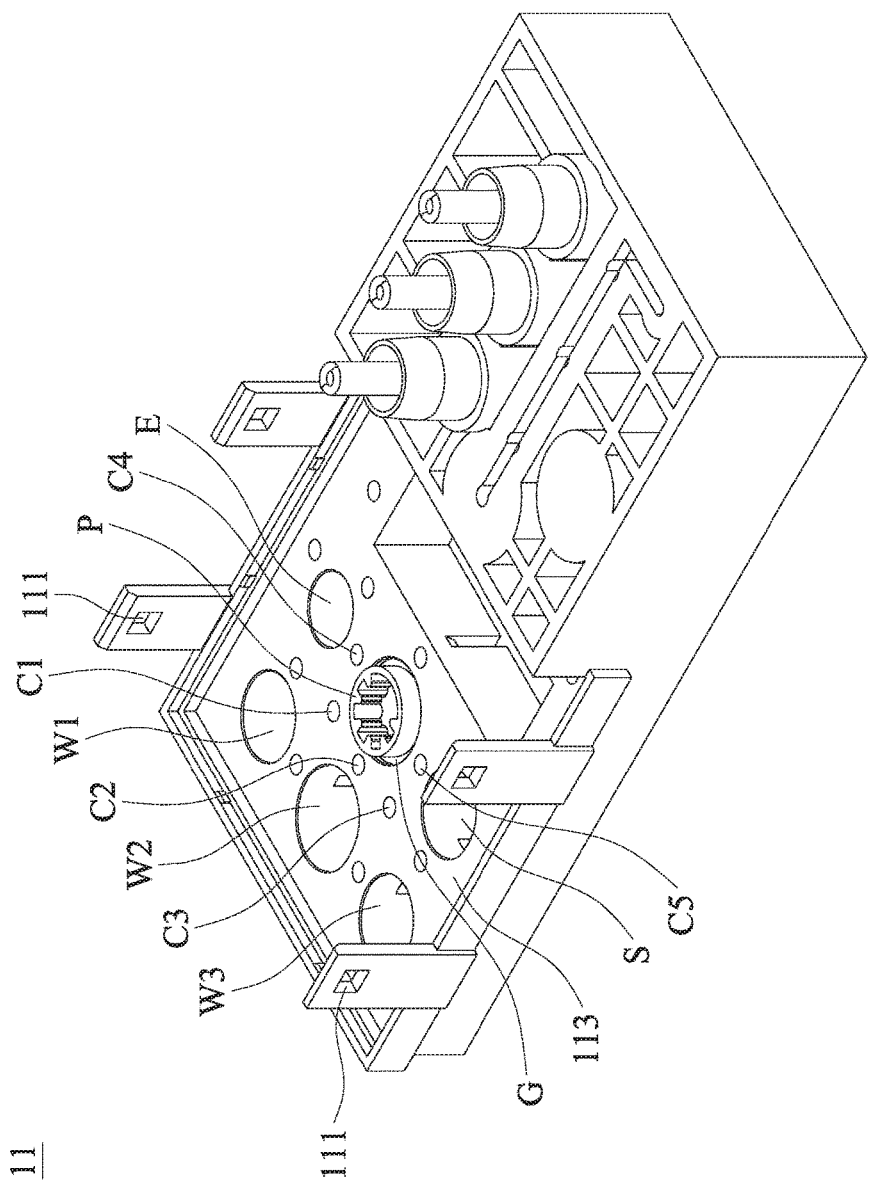
Figure 2C:
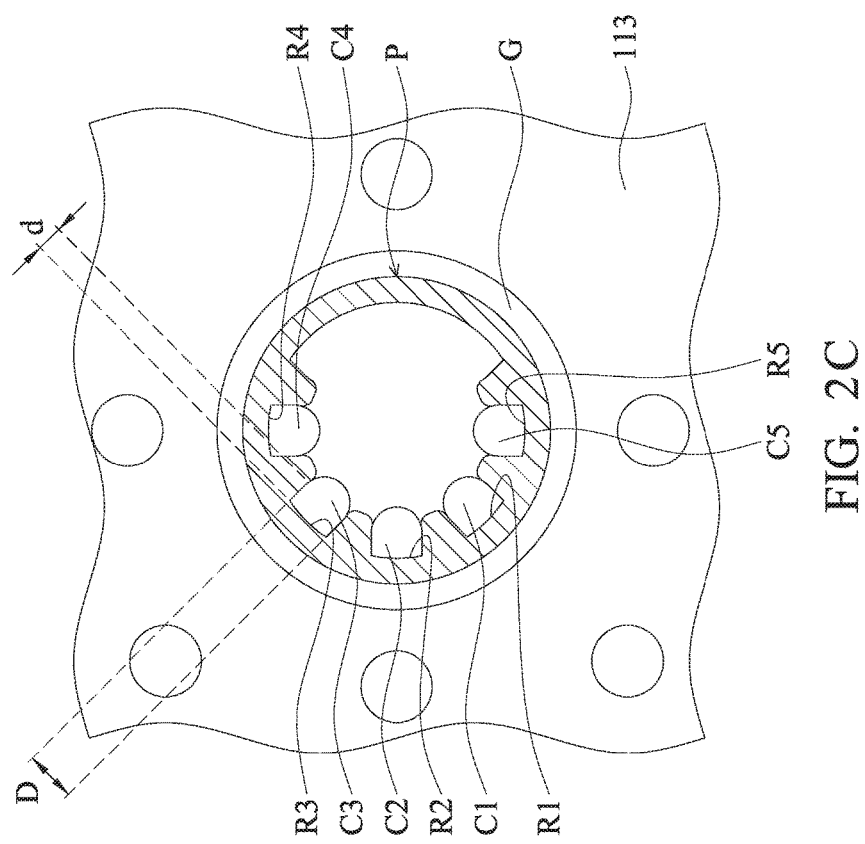
FIG. 2C is an enlarged bottom view of the guide portion P in FIG. 2B.

As shown in FIGS. 2B and 2C, the annular and hollow guide portion P is disposed on a lower side of the upper member 11. In this embodiment, the guide portion P protrudes from the bottom surface 113 of the upper member 11 and communicates with the cleaner channels C1-C3, the sample channel C4, the elution channel C5, and the nucleic acid capturing chamber P'. Specifically, several recesses R1-R5 are formed on an inner surface of the guide portion P (FIG. 2C), corresponding to the cleaner channels C1-C3, the sample channel C4, and the elution channel C5 respectively. It can be seen clearly in FIG. 2C that all the recesses R1-R5 have a bottom surface with a width D and two sidewalls with a width d, adjacent to the bottom surface, wherein D>d. With the recesses R1-R5 formed on the inner surface of the guide portion P, the fluid can be efficiently and smoothly guided to the nucleic acid capturing chamber P', to prevent contamination due to backflow or overflow of the fluids between different channels.

Figure 4A:
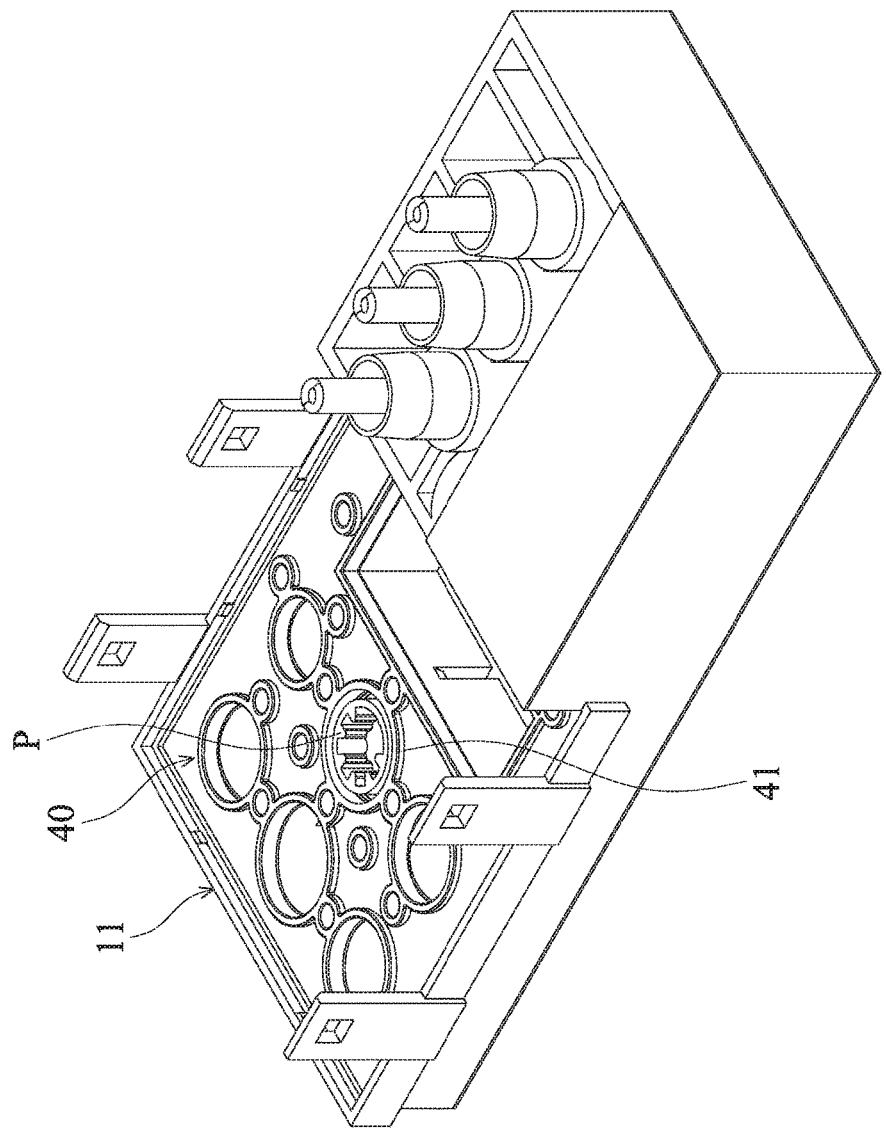
FIG. 4A is a perspective diagram of the upper member and the buffer member assembled to each other.
Figure 4B:
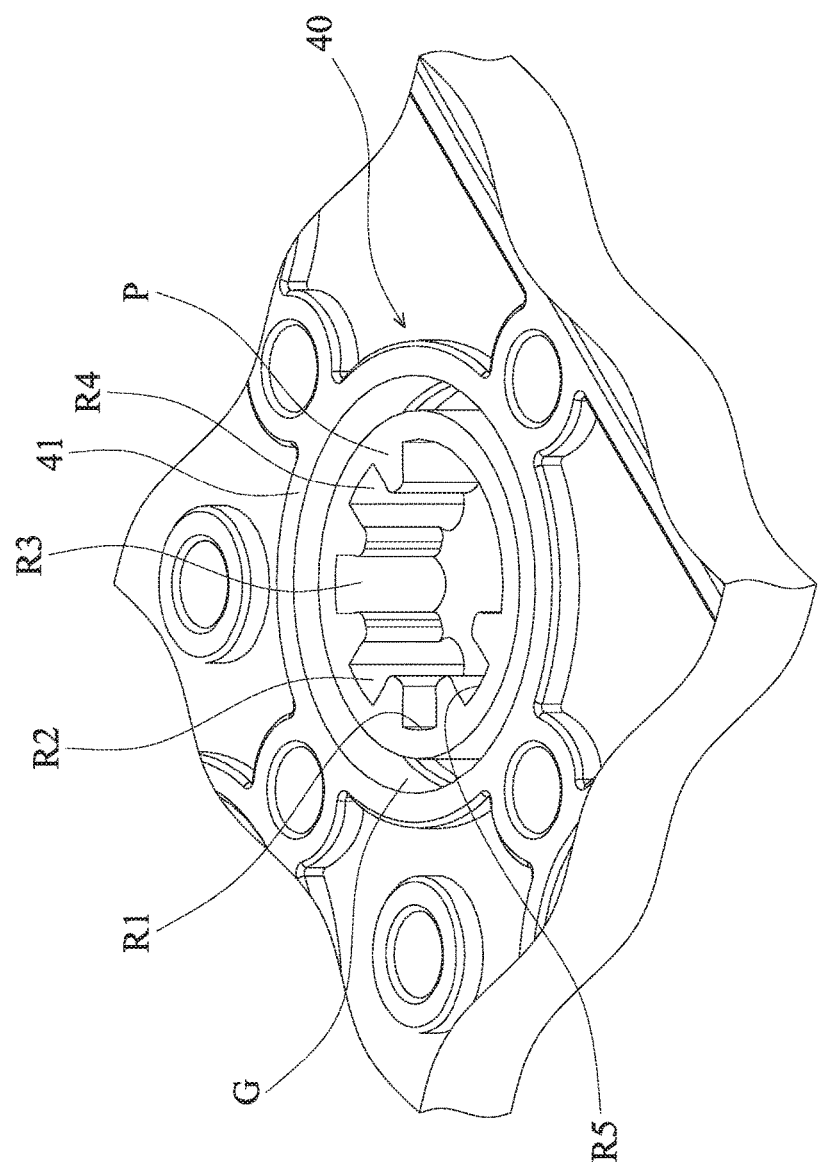
FIG. 4B is a perspective diagram showing a gap disposed between the guide portion and an annular rib on the buffer member.

Referring to FIGS. 4A and 4B, the buffer member 40 is adhered to the bottom surface 113 of the upper member 11, and comprising at least an annular rib 41 surrounding the guide portion P. As shown in FIG. 4B, an annular gap G is formed between the rib 41 and the guide portion P, so as to prevent the fluid from overflowing and spreading to the buffer member 40 when the fluid is guided through the guide portion P, such that the fluid can be completely guided to the nucleic acid capturing chamber P'. In this embodiment, the height of the guide portion P relative to the bottom surface 113 exceeds that the height of the rib 41 relative to the bottom surface 113. Additionally, the buffer member 40 is compressible and can provide a deformation tolerance when clamped by the upper and lower modules 10 and 20, so as to facilitate tight sealing between the upper and lower modules 10 and 20.

In summary, the invention provides a nucleic acid extracting device having an upper module and a lower module which may have even thickness of constructing walls and is easily to be produced by Computer Numerical Control (CNC) machines. Therefore, the nucleic acid extracting device can have the advantages of high structural strength and easy assembling. Moreover, since the main body of the nucleic acid extracting device is assembled by the upper module and the lower module, it is easy to fill elution and cleaner into the reservoirs in the lower module previously. When performing the nucleic acid extraction, it is also easy to load a test sample to the sample reservoir in the lower module before the upper and lower modules are assembled together when performing sample testing, thus facilitating simple assembly and easy use. Furthermore, as the nucleic acid extracting device of the invention has the advantages of small dimensions, high accuracy, and instant diagnosis, it can also be used as a medical detection platform to implement Point of Care (POC) and In Vitro Diagnostics (IVD).

While the invention has been described by way of example and in terms of preferred embodiment, it is to be understood that the invention is not limited thereto. On the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. A nucleic acid extracting device, comprising:
   a lower module, having a sample reservoir, an elution reservoir, and a nucleic acid capturing chamber, wherein a sample is received in the sample reservoir, and an elution is received in the elution reservoir;
   a material for capturing nucleic acid, disposed in the nucleic acid capturing chamber; and
   an upper module, having a sample channel that communicates with the sample reservoir, and an elution channel that communicates with the elution reservoir, wherein the nucleic acid capturing chamber communicates with the sample channel and the elution channel;
   a flexible buffer member disposed between the upper module and the lower module to form an annular rib;
   wherein the sample enters the nucleic acid capturing chamber via the sample channel, a nucleic acid in the sample is absorbed by the material, and the elution enters the nucleic acid capturing chamber via the elution channel to wash the nucleic acid out of the nucleic acid capturing chamber;
   wherein the upper module further has a bottom surface facing toward the lower module, and an annular guide portion protruding from the bottom surface and facing toward the nucleic acid capturing chamber, wherein the elution channel communicates the elution reservoir with the guide portion, the annular rib surrounds the guide portion with a gap formed therebetween, and the height of the guide portion relative to the bottom surface exceeds the height of the rib relative to the bottom surface;
   wherein the sample channel communicates the sample reservoir with the guide portion, and an inner surface of the guide portion forms a plurality of recesses corresponding to the sample channel and the elution channel respectively, wherein each of the recesses forms a bottom and two sidewalls on opposite sides of the bottom to fluidly isolate the recesses from each other, and the width of the bottom exceeds the widths of the sidewalls.

2. The nucleic acid extracting device as claimed in claim 1, wherein the nucleic acid extracting device further comprises a hollow member forming a tubular body with the material disposed therein for capturing the extracted nucleic acid, and the tubular body has a tapered inlet and a tapered outlet which are tapered along a flow direction of the tubular body.

3. The nucleic acid extracting device as claimed in claim 1, wherein the upper module further has an upper member and an upper membrane, and the upper membrane is adhered to the upper member and adjacent to the sample channel and the elution channel.

4. The nucleic acid extracting device as claimed in claim 1, wherein the lower module further has a lower member and a lower membrane adhered to the lower member.

5. The nucleic acid extracting device as claimed in claim 1, wherein the lower module further has a waste liquid reservoir, and the upper module further has a waste liquid channel that communicates with the nucleic acid capturing chamber and the waste liquid reservoir, wherein a fluid flows from the nucleic acid capturing chamber through the waste liquid channel to the waste liquid reservoir.

6. The nucleic acid extracting device as claimed in claim 1, wherein the lower module further has a cleaner reservoir, and the upper module further has a cleaner channel that communicates with the cleaner reservoir and the nucleic acid capturing chamber, wherein a cleaner flows from the cleaner reservoir through the cleaner channel to the nucleic acid capturing chamber.

7. The nucleic acid extracting device as claimed in claim 1, wherein the upper module further has a first joining portion, and the lower module further has a second joining portion joined to the first joining portion when the upper module and lower module are assembled.

8. The nucleic acid extracting device as claimed in claim 1, wherein the lower module further has a nucleic acid collection channel, and the upper module further has a nucleic acid collection reservoir that communicates with the nucleic acid collection channel, wherein the elution with extracted nucleic acid flows through the nucleic acid collection channel to the nucleic acid collection reservoir.

9. The nucleic acid extracting device as claimed in claim 8, further comprises a container detachably connected to the upper module for receiving the elution with extracted nucleic acid.

10. The nucleic acid extracting device as claimed in claim 1, further comprises a plurality of air channels extended through the upper module and lower module, to respectively push the sample and the elution by pneumatic pressure into the nucleic acid capturing chamber.

* * * * *